(12) United States Patent
Klardie et al.

(10) Patent No.: US 9,550,056 B2
(45) Date of Patent: Jan. 24, 2017

(54) MEDICAL LEADS AND RELATED SYSTEMS THAT INCLUDE A LUMEN BODY THAT IS JOINED TO A LEAD BODY AND THAT HAS MULTIPLE FILAR LUMENS

(71) Applicant: MEDTRONIC, INC., Minneapolis, MN (US)

(72) Inventors: Michael R. Klardie, Bloomington, MN (US); Michael J. Kern, St. Louis, MO (US); Brian T. Stolz, Boomington, MN (US); Marty D. Martens, Bloomington, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 116 days.

(21) Appl. No.: 14/444,970

(22) Filed: Jul. 28, 2014

(65) Prior Publication Data
US 2014/0336740 A1    Nov. 13, 2014

Related U.S. Application Data

(62) Division of application No. 14/138,204, filed on Dec. 23, 2013, now Pat. No. 8,792,995, which is a division
(Continued)

(51) Int. Cl.
*A61N 1/04* (2006.01)
*A61N 1/05* (2006.01)
*A61N 1/08* (2006.01)

(52) U.S. Cl.
CPC .............. *A61N 1/05* (2013.01); *A61N 1/056* (2013.01); *A61N 1/0551* (2013.01); *A61N 2001/086* (2013.01); *Y10T 29/49204* (2015.01)

(58) Field of Classification Search
CPC ........ A61N 1/048; A61N 1/0488; A61N 1/05; A61N 1/3752; A61N 1/056; A61N 1/0563; A61B 2017/22021; A61B 2562/22
See application file for complete search history.

(56) References Cited

U.S. PATENT DOCUMENTS 5,458,629 A * 10/1995 Baudino ................. A61N 1/056
                                                        600/396
6,253,111 B1 * 6/2001 Carner .................... A61N 1/056
                                                        600/373
(Continued)

*Primary Examiner* — Christopher D Koharski
*Assistant Examiner* — Natasha Patel
(74) *Attorney, Agent, or Firm* — Withers & Keys, LLC

(57) ABSTRACT

Medical leads include a lumen body at an end of the lead, and the lumen body includes multiple filar lumens. The lumen body is joined to a lead body, and electrical connectors are longitudinally spaced along the lumen body. Filars within the filar lumens are directed through filar passageways within the lumen body to attach to the electrical connectors on the lumen body. The filar passageways may be aligned with the filar lumens, and slots within the electrical connectors may be aligned with the filar passageways to facilitate assembly. The lumen body may provide additional stiffness to the end of the lead where the lumen body is located to facilitate lead insertion into the medical device. The filar lumens of the lumen body may have a longitudinally straight configuration so that the portions of filars within the filar lumens are held in a longitudinally straight configuration.

13 Claims, 23 Drawing Sheets

Related U.S. Application Data of application No. 13/932,107, filed on Jul. 1, 2013, now Pat. No. 8,634,936, which is a division of application No. 13/070,593, filed on Mar. 24, 2011, now Pat. No. 8,478,425.

(60) Provisional application No. 61/319,848, filed on Mar. 31, 2010.

(56) References Cited

U.S. PATENT DOCUMENTS

| | | | |
|---|---|---|---|
| 6,792,317 B1* | 9/2004 | Doan | A61N 1/056 607/122 |
| 2006/0095107 A1* | 5/2006 | Osypka | A61N 1/056 607/122 |

* cited by examiner

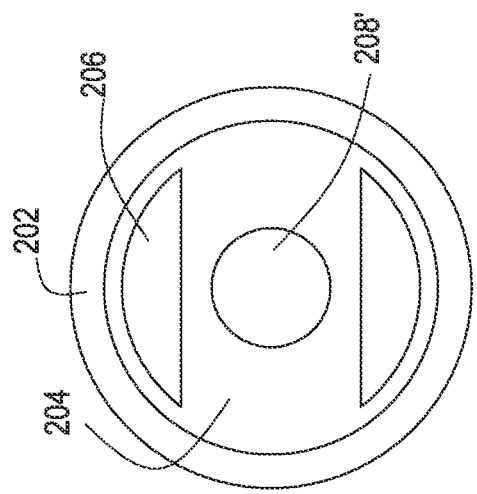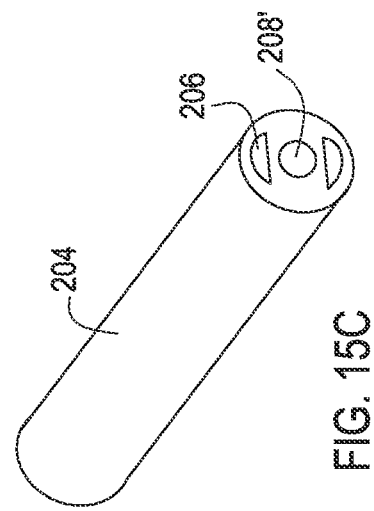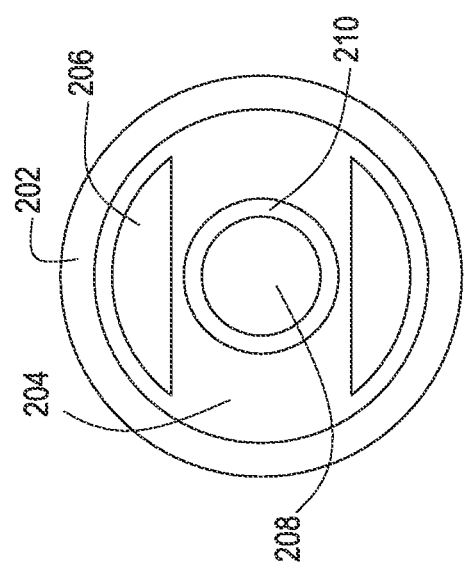

MEDICAL LEADS AND RELATED SYSTEMS THAT INCLUDE A LUMEN BODY THAT IS JOINED TO A LEAD BODY AND THAT HAS MULTIPLE FILAR LUMENS

CROSS-REFERENCE TO RELATED APPLICATION

The present application claims priority to U.S. Provisional Patent Application No. 61/319,848, filed Mar. 31, 2010, which application is hereby incorporated by reference as if re-written in its entirety.

TECHNICAL FIELD

Embodiments relate to medical leads and systems that utilize medical leads. More particularly, embodiments relate to medical leads that include a lumen body that is joined to a lead body while the lumen body provides multiple filar lumens.

BACKGROUND

Medical leads often include multiple filars that carry electrical signals between electrical circuitry of medical devices and electrodes on a distal end of the medical leads. The filars extend from connectors on a proximal end of the medical leads to the electrodes on the distal end.

During construction of the medical leads, the filars are initially placed within an interior of a lead body. In many cases, the lead body includes a central lumen and the filars are present within the central lumen. The filars within the central lumen may be coiled to offer flexibility and extendibility to the lead. The filars must be brought into physical contact with the electrical connectors and electrodes on the proximal and distal ends of the leads. This is largely a manual task where a technician must cut a slit in the lead body, select a filar, and pull the filar through the slit. The filar is then physically attached to the electrode that is placed over the lead body nearby the slit.

Selecting the filar and pulling it through the slit can be a burdensome task, especially where the filars are coiled within the lead body. Where the filars are coiled, the technician must first unwind the filars over a certain length so that the filars can be individually grasped to pull through the appropriate slit in the lead body. The more burdensome the task of assembling the medical leads, the more costly the process in terms of the amount of time spent per lead.

Once a medical lead is constructed, it is then used in practice by being inserted into a medical device by a clinician during the installation of the medical device for a patient. When installing the medical lead, the clinician grasps the proximal end and inserts the proximal end into a port of the medical device. The stiffness of the proximal end of the lead affects the amount of insertion force that may be supplied. If the proximal end is not adequately stiff, the clinician may have trouble properly inserted the lead. However, if the whole lead body is stiff, then routing the lead body to the stimulation site within the patient becomes difficult and the lead is more susceptible to movement and damage due to movements of the patient.

SUMMARY

Embodiments address one or more of these issues and others by providing a lead. having a lumen body joined to the lead body where the lumen body includes multiple filar lumens. The multiple filar lumens may house individual filars while the lead body may include fewer lumens than the lumen body. The multiple filar lumens of the lumen body may be longitudinally straight where the filars within the filar lumens are also longitudinally straight while being coiled in the lead body. The lumen body may be present at the proximal end and have a stiffness greater than the lead body so that the proximal end of the lead has increased stiffness. Furthermore, the lumen body may be used as a tool to maintain the proximal ends of the filars in a longitudinally straight configuration while the remaining portion of the filars is being coiled with the lumen body then forming a proximal end. substructure during subsequent lead assembly.

DESCRIPTION OF THE DRAWINGS

FIG. 15A shows a transverse cross-sectional view of a second alternate lumen body that has a stiffener for the medical lead example.

FIG. 15B shows a transverse cross-sectional view of an alternative second alternate lumen body for the medical lead example that lacks a stiffener.

FIG. 15C shows a perspective view of the lumen body of FIG. 15A.

DETAILED DESCRIPTION

Embodiments provide medical leads and related medical systems that include a lumen body that has multiple filar lumens. The lumen body is present at an end of the lead where electrical connectors are present and the lumen body is joined to a lead body forming the remainder of the medical lead. The lumen body may have more filar lumens than the lead body and/or may have a different stiffness than the lead body. The lumen body may also have longitudinally straight filar lumens so that the ends of filars of the medical lead that are present within the filar lumens are also longitudinally straight.

Figure 1:
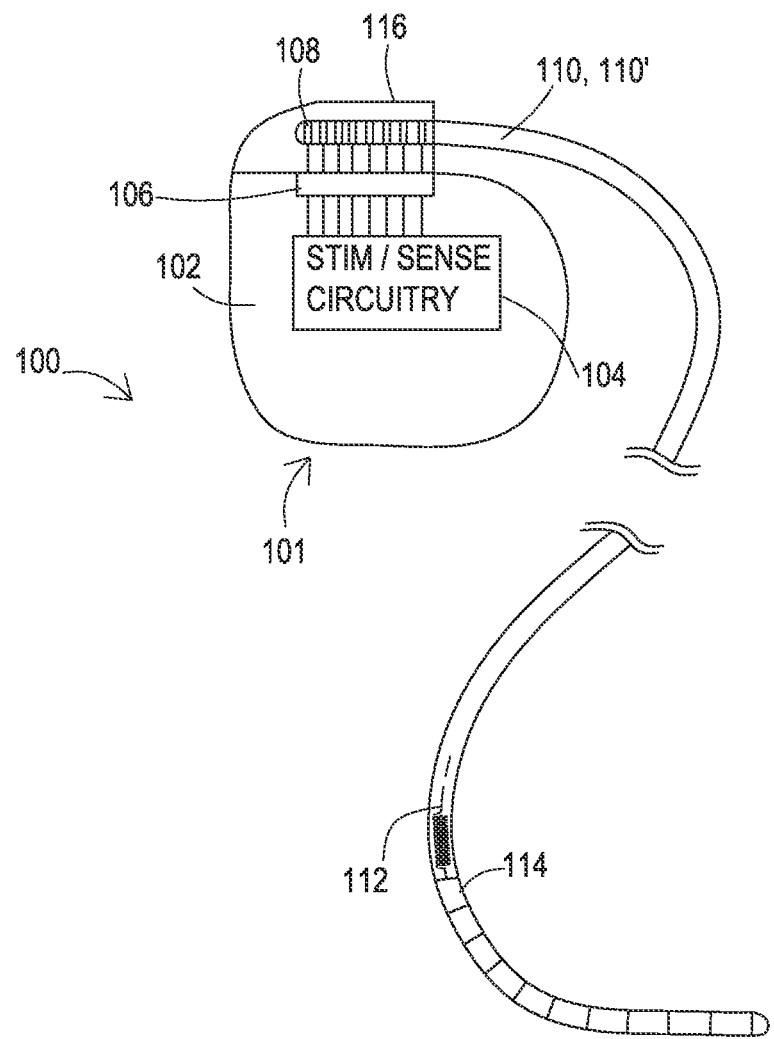
FIG. 1 shows a medical system including an implantable medical device and an implantable medical lead according to various embodiments.

FIG. 1 shows a medical system 100 that includes an implantable medical device 101 and an implantable medical lead 110, 110'. The implantable medical device 101 includes a housing 102 that contains circuitry 104 for providing medical tasks such as stimulation or physiological sensing. The circuitry 104 includes electrical interconnections to a feedthrough 106 that passes the electrical signals to contacts 108 within a header block 116 of the medical device 101. The contacts 108 are where connectors of the header block 116 contact connectors of the medical lead 110, 110'.

The medical lead includes conductors 112 which are coils in this example. These conductors 112 carry signals between the connections 108 within the header block 116 and electrodes 114 on a distal end of the medical lead 110, 110'. These electrodes 114 may be used to deliver stimulation signals being generated by the circuitry 104 to adjacent tissue of a patient and/or to sense physiological signals from the adjacent tissue and provide those to the circuitry 104.

Figure 2:
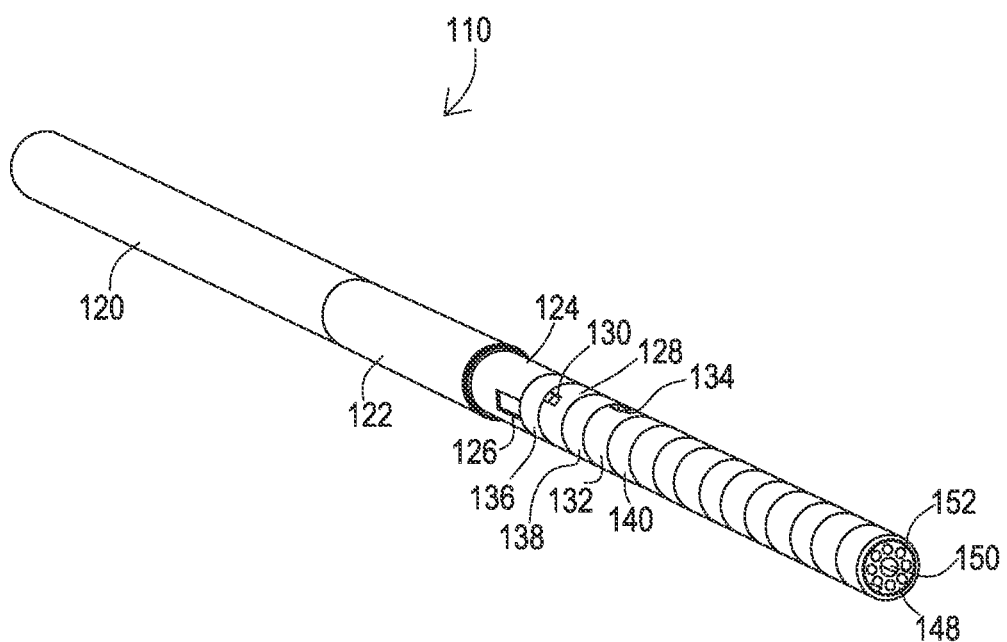
FIG. 2 shows a proximal end of an example of the medical lead example.

FIG. 2 shows a proximal end of an example of the medical lead 110. This proximal end is ultimately inserted into the medical device 101 during installation of the medical device 101 and the medical lead 110. The medical lead 110 includes an outer jacket layer 120 that spans from the distal end of the lead up to this proximal end as shown. In this particular example, the medical lead 122 also includes an outer tubing 122 that forms a lap joint with inner layers for examples of the medical lead 122 that are shielded so as to be conditionally safe for exposure to magnetic resonance imaging (MRI) scans.

A clink 124 is present on the proximal end and abuts the outer tubing 122 of the lead body. For embodiments where a lap joint is not needed such as because a shield is not present, the outer jacket layer 120 may abut the clink 124 directly. The clink 124 is the final electrical connector that is inserted into the header block 116 of the medical device 101 and may contact seals within the header block 116 to seal the port within the header block 116 that has received the proximal end of the lead 110.

Proximal to the clink 124 are insulative spacers 136, 138, 140, and so on. These insulative spacers separate each of the electrical connectors 128, 132 and so on that are present. The electrical connectors 128, 132 make contact with the electrical contacts within. the header block 116.

The proximal clink 124; insulative spacers 136, 138, and 140; and the electrical connectors 128, 132 are all placed on a lumen body 148 that extends to the proximal tip of the lead 110. The lumen body 148 contains multiple filar lumens 152 and also includes a central lumen 150 that may receive a stylet when the lead is being routed to the stimulation site prior to insertion into the header block 116. The proximal clink 124; insulative spacers 136, 138, and 140; the electrical connectors 128, 132, and the lumen body 148 are all discussed in more detail below.

Figure 3:
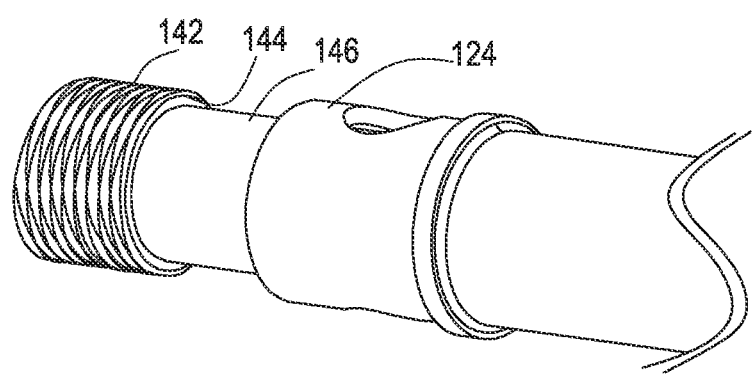
FIG. 3 shows the proximal end of the medical lead example with an outer layer and an outer tubing of the lead body removed to reveal a shield, an inner layer, and an inner tubing.

FIG. 3 shows the proximal end where the lead body encounters the distal end of the clink 124. In this view, the outer tubing 122 and outer jacket layer 120 have been removed to reveal a braided shield 142 that is wrapped about an inner jacket layer 144. In this example where a lap joint is present at the termination of the shield 142, an inner tubing 146 of the lead body extends from the inner jacket layer 144 into the clink 124. For other embodiments such as those where a shield is not present, the inner jacket layer 144 may be integral with the outer jacket layer 120 such that the jacket as a whole enters the clink 124.

Figure 4:
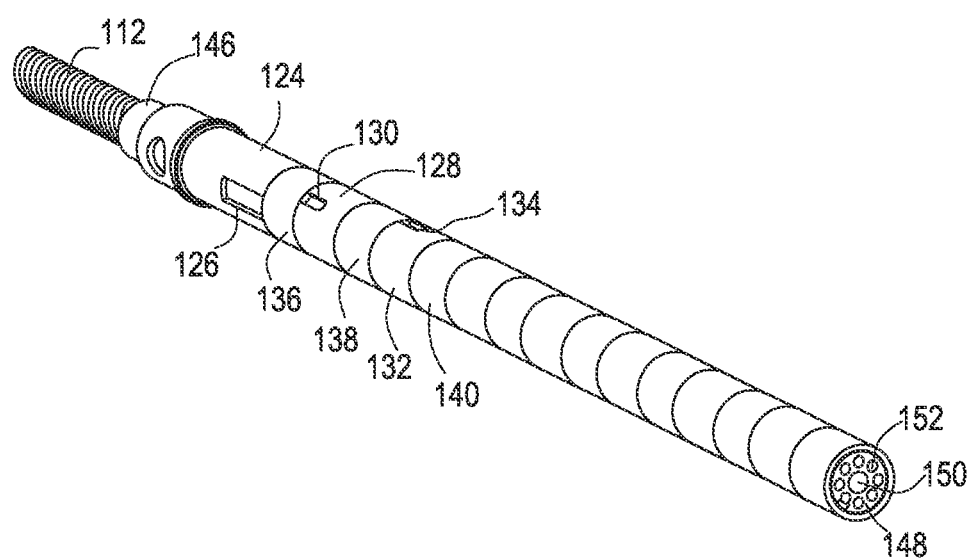
FIG. 4 shows the proximal end of the medical lead example with an inner layer of the lead body removed to reveal a coiled set of filars.

FIG. 4 shows the proximal end with the shield 142 and the inner jacket layer 144 removed to reveal coiled filars 112 entering the inner tubing 146 which is partially contained within the clink 124. This view illustrates that the clink 124 has a proximal slot 126 where a filar can be received and connected via a weld or other form of attachment. This view also illustrates that the electrical connectors 128, 132 which are longitudinally spaced also have distal slots 130, 134 where a filar can be received and connected via a weld or other form of attachment. As can be seen, the slots 126, 130, and 134 are offset circumferentially from each other about the proximal end.

Figure 5:
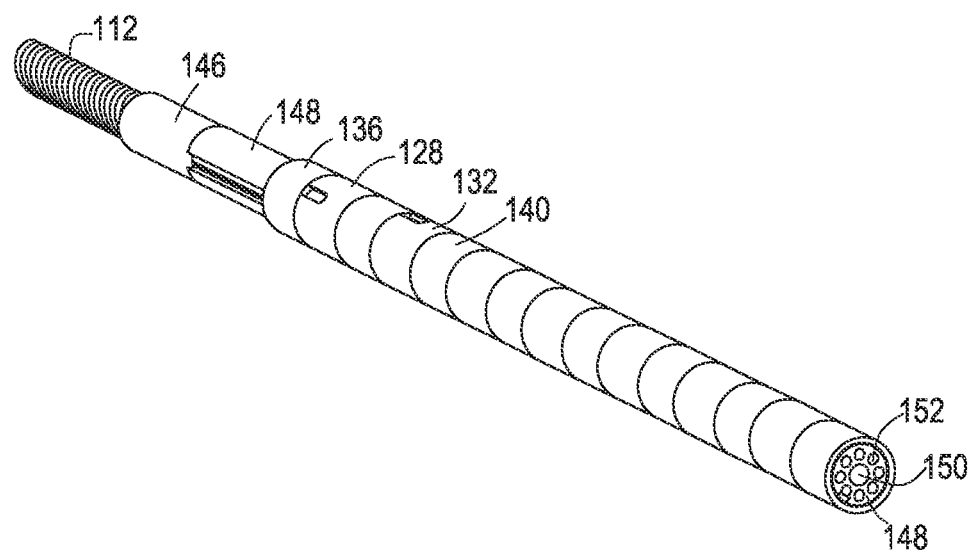
FIG. 5 shows the proximal end of the medical lead example with a clink removed to reveal the inner tubing of the lead body joining a lumen body.

FIG. 5 shows the proximal end with the clink 124 removed to reveal the inner tubing 146 of the lead body abutting the distal end of the lumen body 148. As noted above, the outer tubing 122 of the lead body resides over the abutment of the inner tubing 146 to the lumen body 148 and overlaps the end of the clink 124. In examples where a lap joint is not present, then the jacket layer(s) 120, 144 of the lead body may abut and/or overlap with the lumen body 148.

Figure 6:
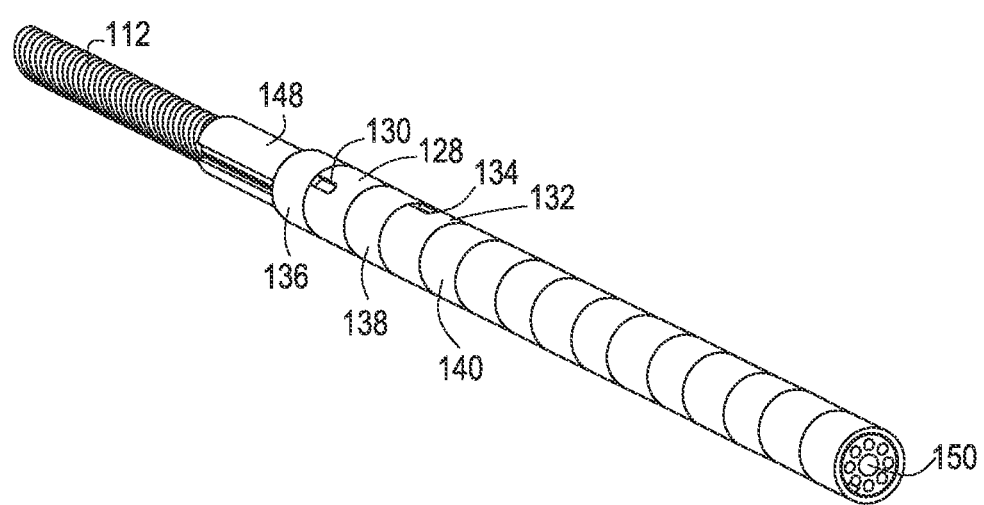
FIG. 6 shows the proximal end of the medical lead example with the inner tubing removed to reveal the coiled set of filars entering the lumen body.

FIG. 6 shows the proximal end with the inner tubing 146 removed to reveal the coiled Mars 112 continuing to the distal end of the lumen body 148 where the filars then enter the lumen body 148. At that point, each filar 112 enters a filar lumen 152 and extends in the proximal direction in a longitudinally straight configuration.

Figure 7:
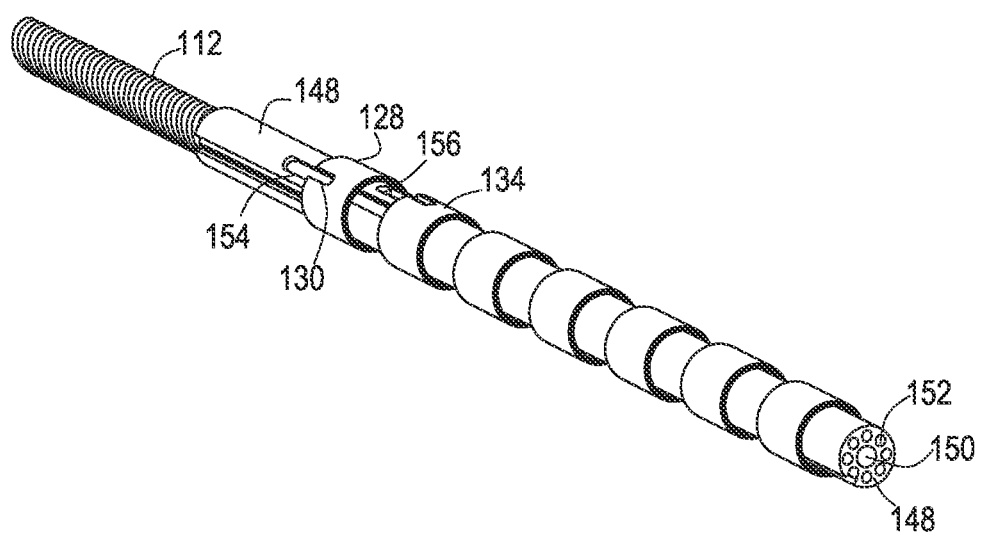
FIG. 7 shows the proximal end of the medical lead example with spacers between connectors removed.

FIG. 7 shows the proximal end of the lead 110 with the spacers 136, 138, 140 and so on removed to reveal the lumen body 148 between each of the electrical connectors 128, 132. Each electrical connector 128, 132 is aligned so that the slot 130, 134 of the electrical connector is aligned with a corresponding filar passageway 154, 156 within the lumen body 148. Each filar passageway 154, 156 provides a pathway for a filar 112 to exit the particular filar lumen 152 that it resides within and enter the slot 154, 156 of the appropriate electrical connector 128, 132 to which the filar should be electrically connected. The filar passageway 154, 156 may be a slit made by a knife or other cutting manual instrument or may be a hole that has been punched, laser ablated, or otherwise created. Each filar passageway 154, 156 is created in alignment with each corresponding filar lumen 152 such that the filar passageways 154, 156 are offset both longitudinally and circumferentially.

Figure 8:
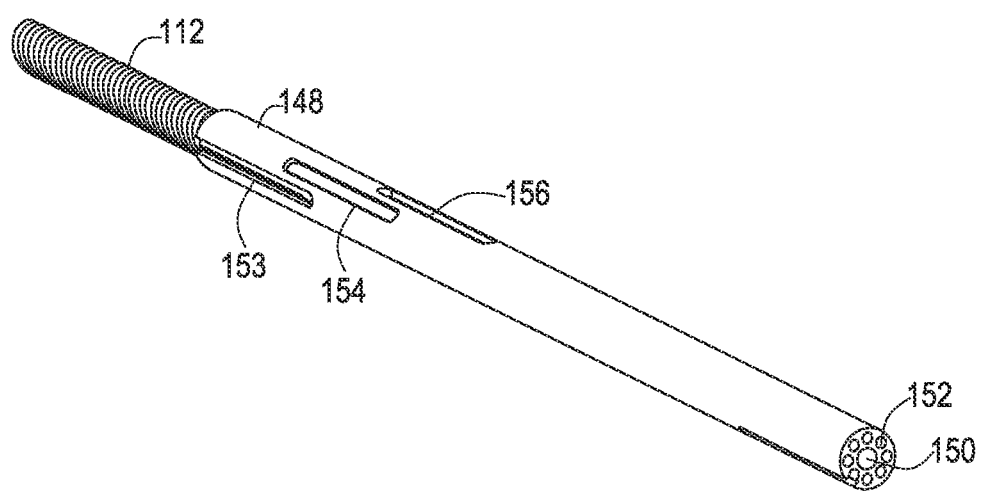
FIG. 8 shows the proximal end of the medical lead example with the connectors removed.

FIG. 8 shows the proximal end of the medical lead with the electrical connectors 128, 132, and so on removed to fully reveal the lumen body 148. As is discussed below, the assembly of the lead 110 may begin after the filars 112 have been coiled in a process that utilizes the lumen body 148 to create longitudinally straight filar ends. In that case, the construction of a subassembly of the coiled filars 112 with the longitudinally straight ends present within the filar lumens 152 of the lumen body 148 as shown in FIG. 8 occurs during the filar coiling process, and this subassembly may then be carried forward to the lead assembly process.

As can be seen in this example, the lumen body 148 may have a length that spans the clink 124 and all connectors on this end of the medical lead 110. As such, the lumen body 148 is a relatively small length compared to the length of the whole medical lead 110 and is much less than half the length of the whole lead 110 in this example. The length of the lumen body 148 in this example is such that the majority of the lumen body 148 is present within the header block 116 upon insertion of the lead 110 into the medical device 101. Therefore, the stiffness added by the lumen body 148 affects only the end region of the lead 110 and does not hinder the routing of the lead to the stimulation site.

Figure 9:
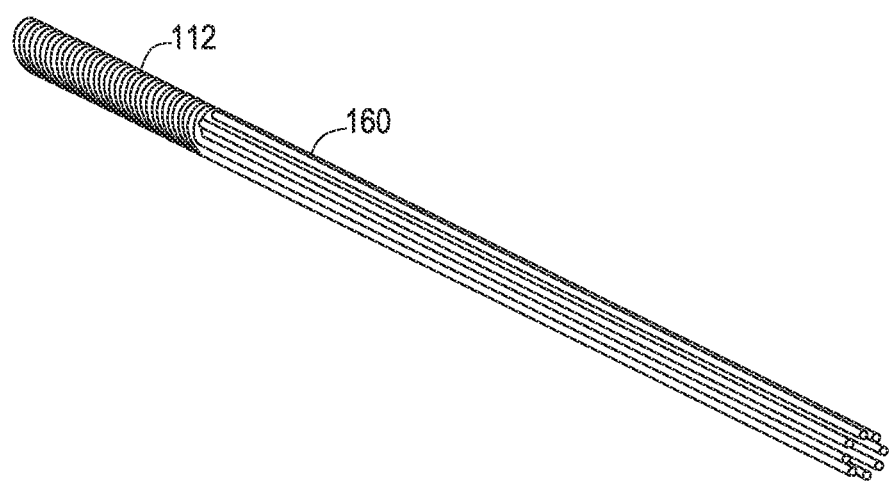
FIG. 9 shows the proximal end of the filars of the medical lead example.

FIG. 9 shows the proximal end of the filars 112 having longitudinally straight ends 160. In the medical lead 110, these longitudinally straight ends 160 are present within the filar lumens 152 of the lumen body 148. In an alternative medical lead 110' that is discussed in more detail below, these longitudinally straight ends 160 may be present within a central lumen of the lead body rather than within filar lumens of the lumen body 148.

Figure 10:
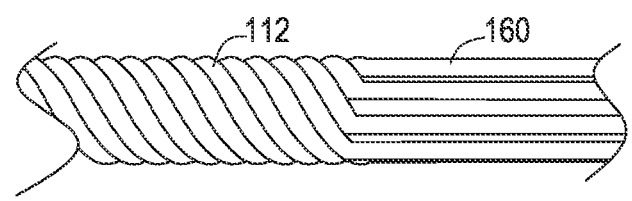
FIG. 10 shows the transition of the filars from being coiled to being longitudinally straight for the medical lead example.

FIG. 10 shows a side view of the filars 112 having the longitudinally straight ends. In this view, it can be seen that the filars are coiled at a constant pitch from a coil starting point at the distal end until reaching a coil end point where the filars transition into the longitudinally straight configuration. This transition may be achieved by use of the lumen body 148 during the coiling process. A coiling tool discussed in more detail below may be used during the coiling process in place of the lumen body 148 for the medical lead embodiments 110' where the lumen body 148 is not present or where it is otherwise not desirable to use the lumen body 148 during the coiling process.

Figure 11:
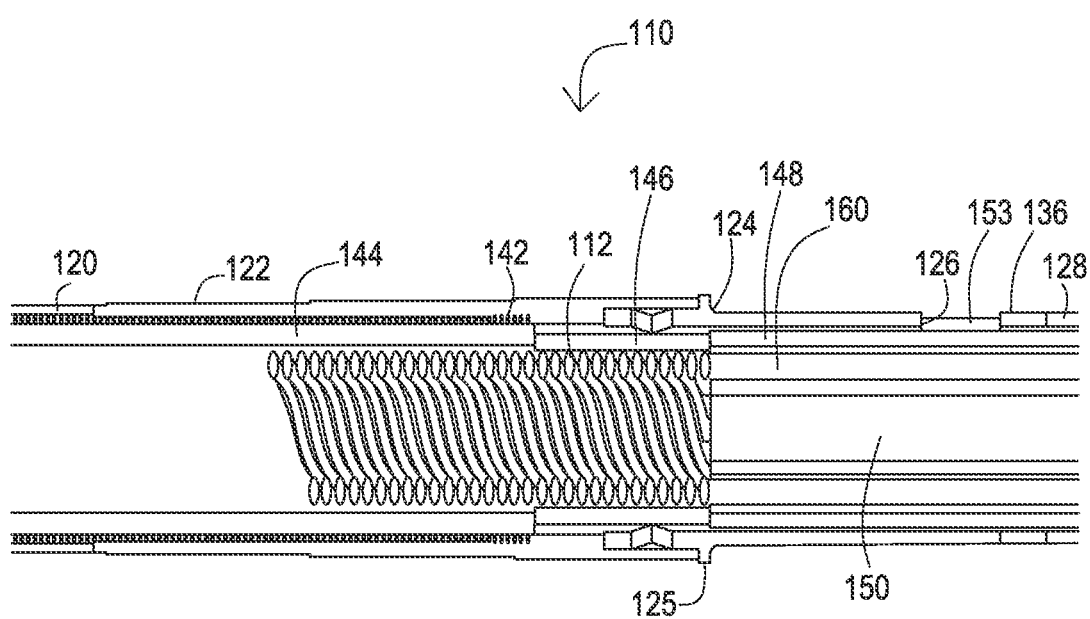
FIG. 11 shows a longitudinal cross-sectional view of the medical lead example.

FIG. 11 shows a longitudinal cross-sectional view of the medical lead embodiments 110, with the view being stretched in the transverse direction of the lead to more clearly illustrate the details of construction. This view shows that the lumen body 148 includes a filar passageway 153 aligned with the slot 126 in the clink 124 to allow one of the filars to exit a filar lumen 152 and connect with the clink 124. In this example, it can be seen that the clink 124 includes a threaded engagement to the inner tubing 146. In this example, the clink 124 also includes a radially extending circumferential flange 125 which abuts the outer tubing 122 as shown.

Figure 12:
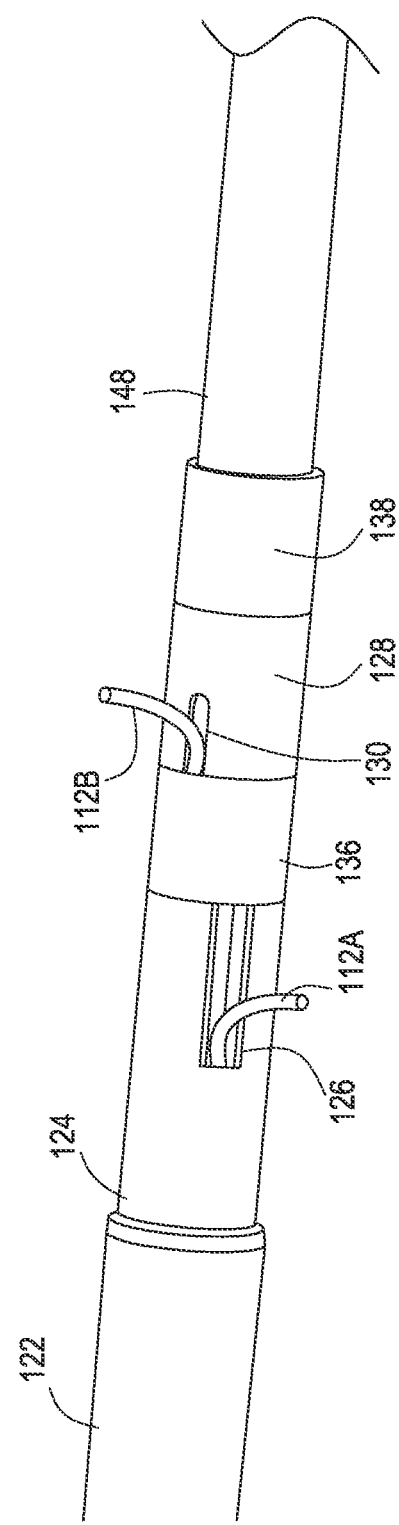
FIG. 12 shows the proximal end of the medical lead during assembly while the filars are being exposed to the connectors.

FIG. 12 shows a view of the proximal end during construction. At this point, the individual filars such as Mars 112A and 112B are being pulled through the filar passageways 154, 156 and slots 126, 130 for attachment to the clink 124 and electrodes 128 and so on. With the ends of the filars already being longitudinally straight, the technician merely pulls a filar already present at a given filar passageway through the slot 126, 130 in the clink 124 or electrode 128 and then creates the bond via a weld or other form of attachment. The technician is relieved from having to unwind the coil and select a particular filar among the group of unwound filars.

Prior to reaching this point of assembly shown in FIG. 12, the medical lead example 110 may be constructed by starting with a lead body where the outer jacket 120 has been ablated to reveal the shield 142 and inner jacket layer 144. A gage pin or stylet may be inserted into the lumen provided by the inner jacket 144 of the lead body, and the inner tubing 146 is placed onto the gage pin and slid into place where the inner tubing 146 is bonded to the inner jacket layer 144.

The outer tubing 122 that provides the lap joint is then placed onto the gage pin and slid into place over the exposed shield 142 and inner tubing 146. The coiled filars 112 with the ends located within the lumen body 148 are then placed onto the gage pin and slid into the lumen of the lead body provided by the inner jacket 144 until the lumen body 148 abuts the inner tubing 146. The inner tubing 146 is bonded to the lumen body 148.

Then the clink 124 is placed onto the lumen body 148 and slid into place with the outer tubing 122 overlapping a shoulder of the clink 124. The clink 124 may be rotated as necessary to align the slot 126 with the filar passageway 153. The first filar 112A is then pulled through the filar passageway 153 with the filar 112A being cut to length with the excess being pulled from the nearest end, in this case from the proximal end. The filar 112A is then bonded to the clink 124.

In some embodiments, the spacer 136 may then be put in place over the lumen body 148 and positioned so that the spacer 136 abuts the clink 124. The spacer 136 may be a pre-formed tubing that is slid onto the lumen body 148 and then reflowed at some time after an adjacent connector 128 is placed onto the lumen body 148 to abut the spacer 136.

In such embodiments, after the spacer 136 has been slid into place, the subsequent connector 128 is slid into place and is rotated as necessary to align the slot 130 with the filar passageway 154. The filar 112B for that electrode is pulled through the filar passageway 154 and slot 130, is cut to length, the excess is pulled from the nearest end, and the filar 112B is bonded to the electrode 128, The next spacer 138 is then put into position adjacent the connector 128 and this continues until all connectors and spacers have been installed. The reflow of the several spacers may occur once all of the spacers and connectors are installed, As an alternative embodiment to reflowing spacers preformed from tubing, the spacers 136, 138, 140 and so on may instead be injection molded onto the lumen body 148. Here, the clink 124 and all connectors 128, 132 and so on may be first installed, and then the gaps between them filled by the injection molding process to create the spacers 136, 138, 140 and so on. Furthermore, the injection molded spacers 136, 138, 140 and so on may be reflowed after injection molding to ensure that the spaces between electrodes are satisfactorily filled.

Figure 13B:
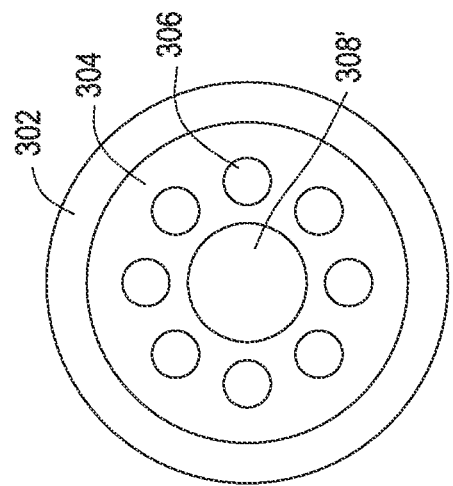
FIG. 13B shows a transverse cross-sectional view of an alternative lumen body for the medical lead example that includes a stiffener.
Figure 13C:
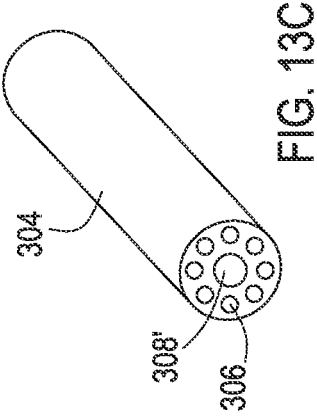
FIG. 13C shows a perspective view of the lumen body of FIG. 13B.
Figure 13A:
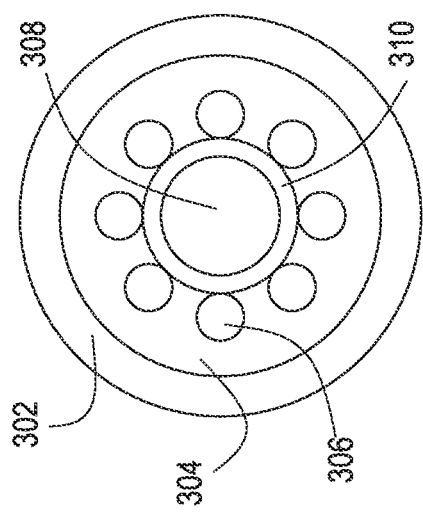
FIG. 13A shows a transverse cross-sectional view of the lumen body for the medical lead example.

FIGS. 13A-13C show one variation for the lumen body. Here, a lumen body 304 may be created within filar lumens 306 of a circular cross-section and a central lumen 308. The lumen body 304 is surrounded by a layer 302 that may represent either a connector or a spacer of a medical lead. In FIG. 13A, a stiffener 310 may be inserted within the central lumen 308 with the stiffener being a stiffening tube to maintain the central lumen 308 for passage of a stylet. The stiffener 310 may be included to provide additional stiffness for the end of the lead where the stiffness added by the presence of the lumen body 304 is less than desired. For instance, the lumen body 304 may be constructed of materials such as 55 Shore D or 75 Shore D biocompatible polymers like thermoplastic polyurethane (TPUR) while the stiffener 310 may be constructed of a stiffer material like 99 Rockwell M or 126 Rockwell M biocompatible polymer like polyetheretherketone (PEEK).

In FIG. 13B and the perspective view of FIG. 13C, the lumen body 304 may provide adequately additional stiffness to the end of the lead for a given application so that no stiffener is necessary, Here, the lumen body 304 may also be constructed of materials such as 55 Shore D or 75 Shore D biocompatible polymers like TPUR.

Figure 14B:
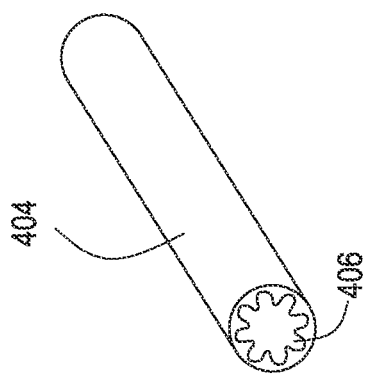
FIG. 14B shows a perspective view of the lumen body of FIG. 14A without the stiffener.
Figure 14C:
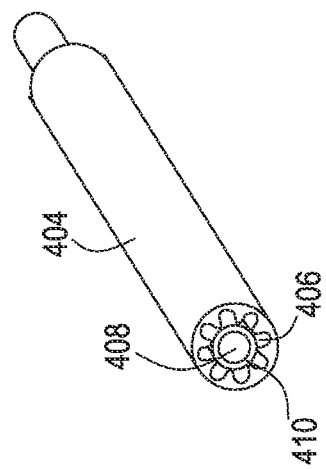
FIG. 14C shows a perspective view of the lumen body of FIG. 14A including the stiffener.
Figure 14A:
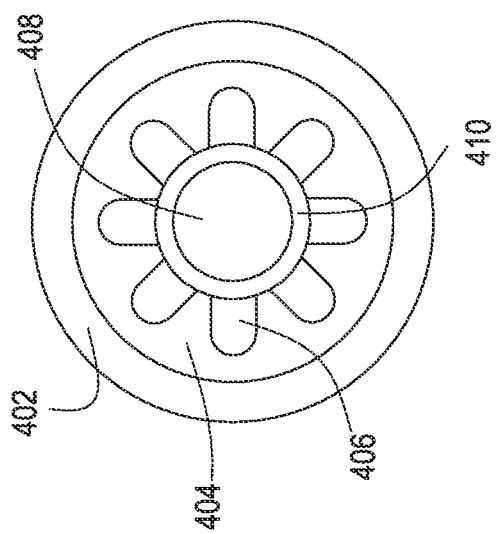
FIG. 14A shows a transverse cross-sectional view of a first alternate lumen body that has a sunflower filar lumen design and a stiffener for the medical lead example.

FIGS. 14A-14C show another variation for the lumen body. Here, a lumen body 404 may be created within filar lumens 406 with a non-circular cross-section so as to create a sunflower cross-section together with a central lumen 408 as shown in FIG. 14B. The lumen body 404 is surrounded by a layer 402 that may represent either a connector or a spacer of a medical lead.

As shown in FIGS. 14A and 14C, a stiffener 410 may be inserted within the central lumen 408 with the stiffener being a stiffening tube to maintain the central lumen 408 for passage of a stylet while creating a barrier to isolate each individual filar lumen 406 from the central lumen 408. Like the example of FIG. 13A above, the lumen body 404 may be constructed of materials such as such as 55 Shore D or 75 Shore D biocompatible polymers like TPUR while the stiffener 410 may be constructed of a stiffer material like 99 Rockwell M or 126 Rockwell M biocompatible polymer like PEEK.

FIGS. 15A-15C show another variation for the lumen body. Here, a lumen body 204 may be created with fewer but larger filar lumens 206 and a central lumen 208, In such a case multiple filar ends may be present within a single filar lumen 206. These filar ends that are grouped within a filar lumen 206 may be longitudinally straight and may be created by using a coiled process and coiling tool discussed below. The lumen body 204 is surrounded by a layer 202 that may represent either a connector or a spacer of a medical lead. In FIG. 15A, a stiffener 210 may be inserted within the central lumen 208 with the stiffener 210 being a stiffening tube to maintain the central lumen 208 for passage of a stylet. Like the example of FIG. 13A above, the lumen body 204 may be constructed of materials such as such as 55 Shore D or 75 Shore D biocompatible polymers like TPUR while the stiffener 210 may be constructed of a stiffer material like 99 Rockwell M or 126 Rockwell M biocompatible polymer like PEEK.

In FIG. 15B and the perspective view of FIG. 15C, the lumen body 204 may be adequately stiff for a given application so that no stiffener is necessary. Like the example of FIG. 13B above, here the lumen body 204 may also be constructed of materials such as 55 Shore D or 75 Shore D biocompatible polymers like TPUR.

While the discussion above regarding the lumen body has been primarily with respect to the proximal end of the medical lead 110, it will be appreciated that the lumen body may additionally or alternatively be located at the distal end, where the discussion of connectors 128, 132 and so on applies to the electrodes of the distal end. The filars 112 may enter the filar lumens 152 of a lumen body 148 present at the distal end, and these liars 112 may have longitudinally straight distal ends within the lumen body 148.

Figure 16:
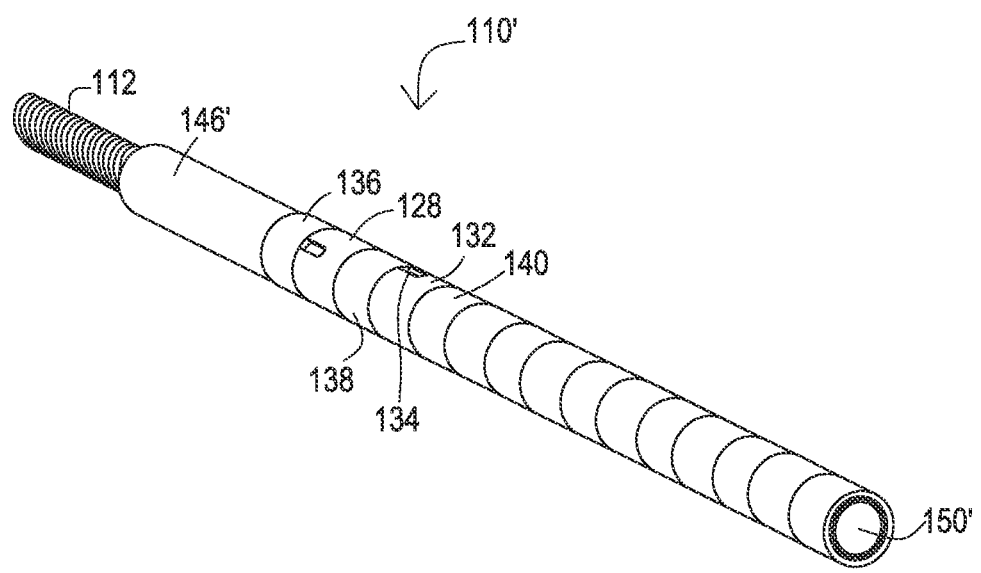
FIG. 16 shows the proximal end of a medical lead example where the proximal ends of the filars are longitudinally straight without a lumen body being present.
Figure 17:
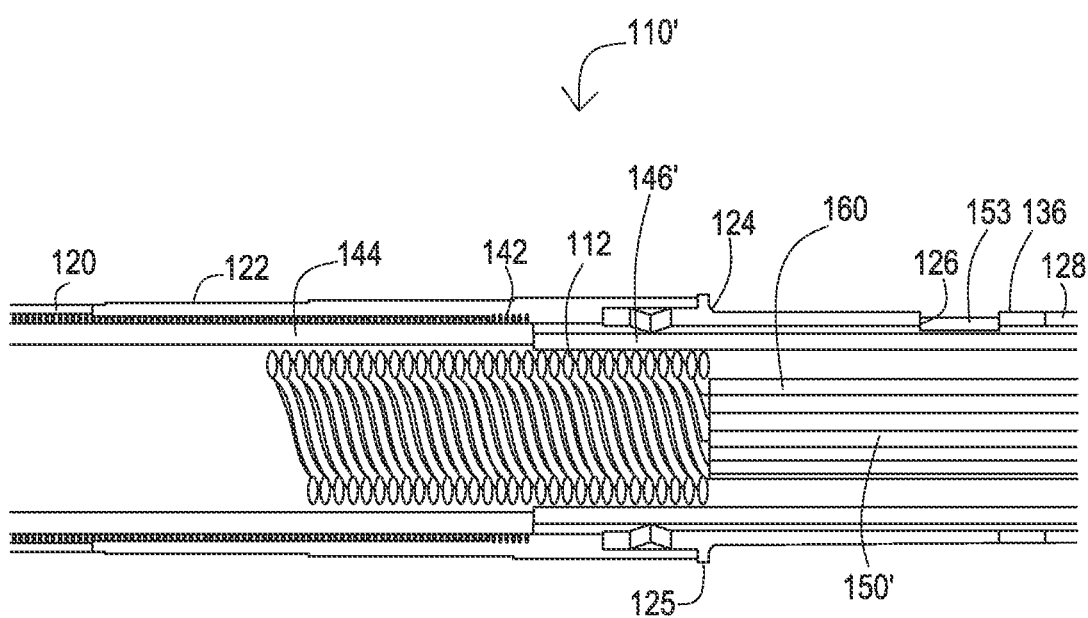
FIG. 17 shows a longitudinal cross-sectional view of the medical lead example of FIG. 16.
Figure 18:
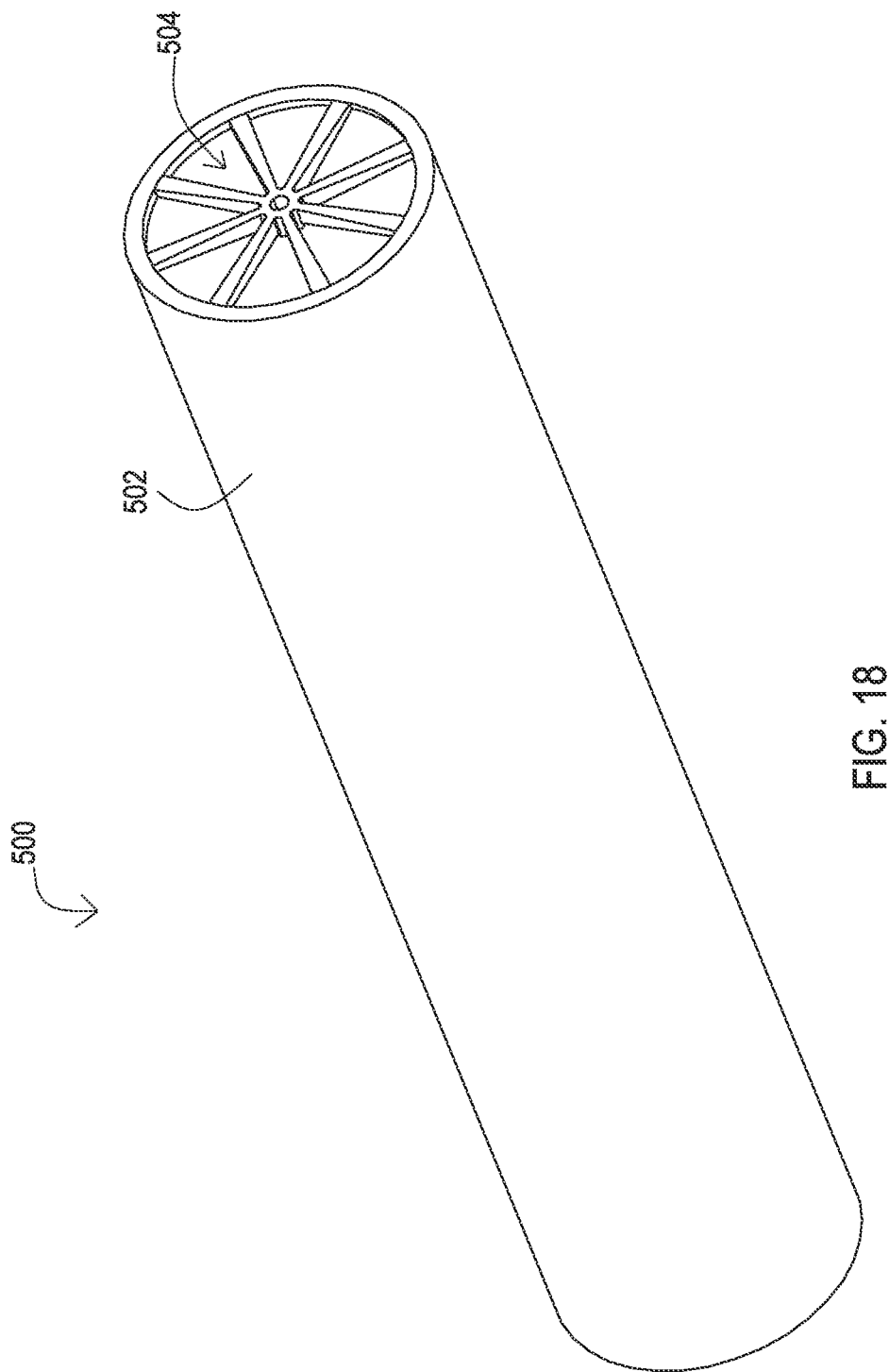
FIG. 18 shows a tool for creating longitudinally straight ends for filars being coiled.
Figure 19:
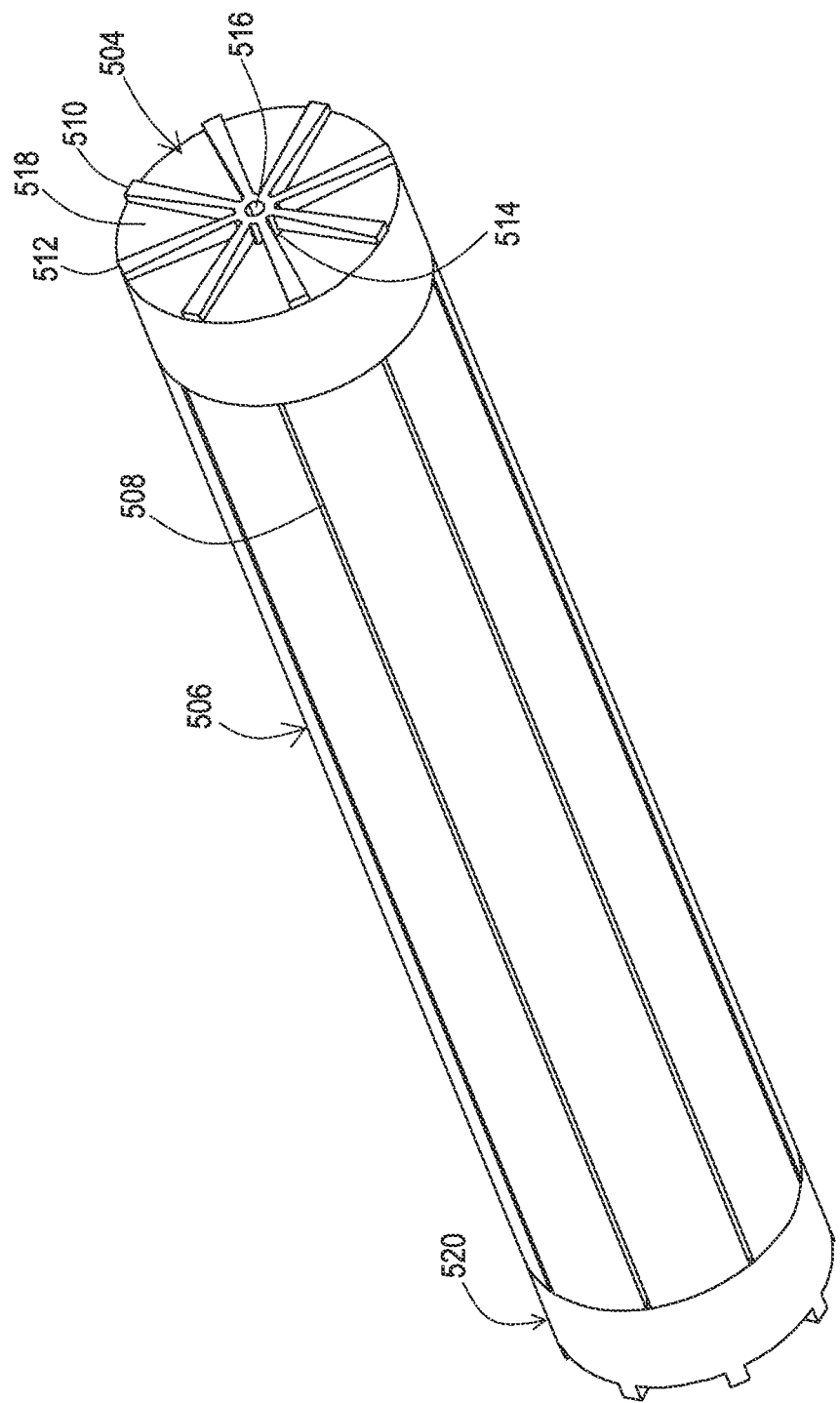
FIG. 19 shows the example of the tool with an outer cover removed.
Figure 20:
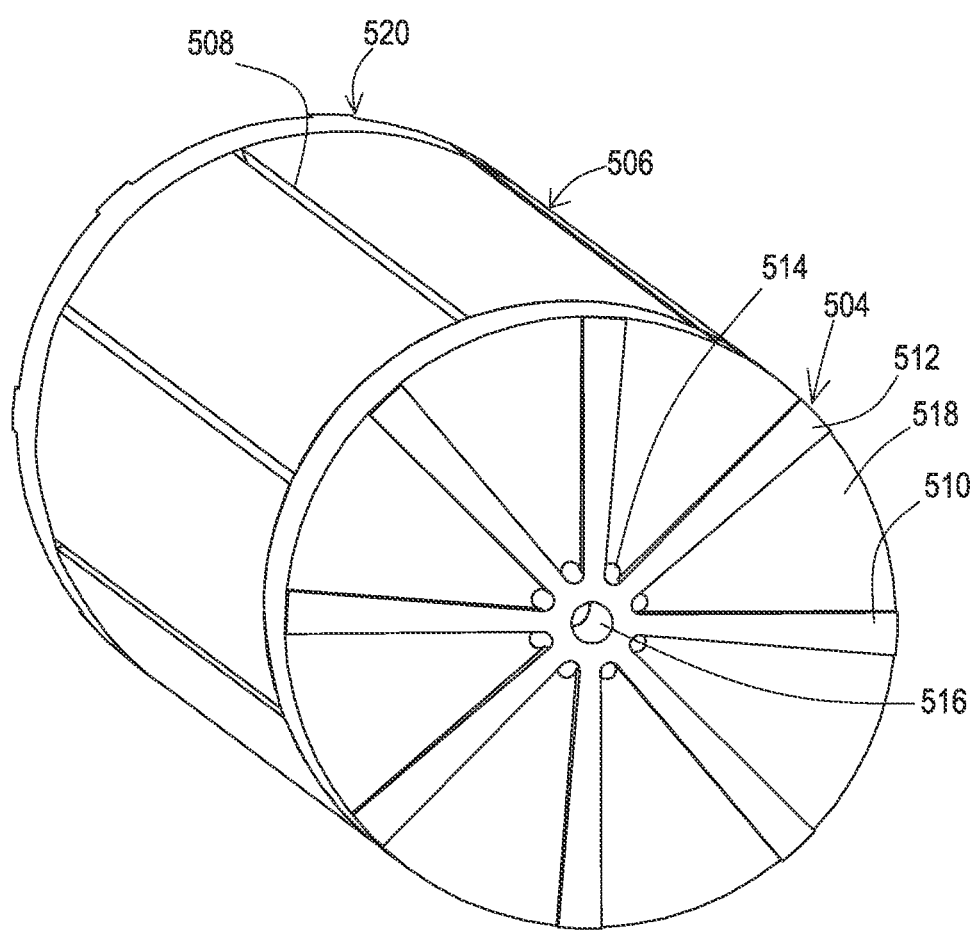
FIG. 20 shows a distal end view of the tool with the outer cover removed.
Figure 21:
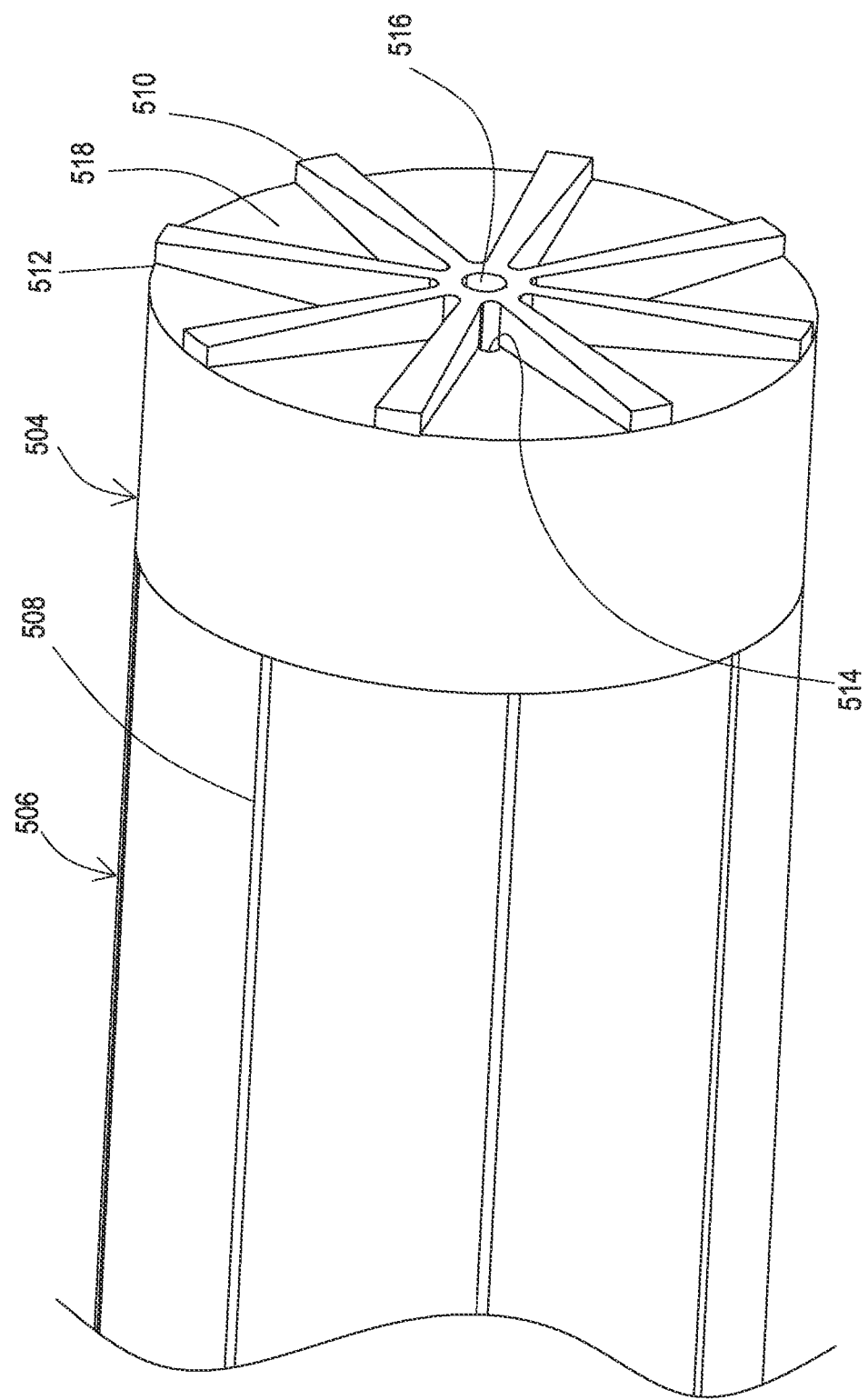
FIG. 21 shows a side view of the distal end of the tool with the outer cover removed.

FIGS. 16 and 17 show views of the medical lead 110' which is an example of medical lead embodiments that lack a lumen body altogether. These alternate medical lead embodiments such as the medical lead example 110' have a lead body layer, such as the inner tubing 146' as shown for the lead 110' or a continuation of the inner jacket layer 144, that continues to the tip of the lead. The filars 112 transition to a longitudinally straight configuration at the clink 124 so that the longitudinally straight portion 160 of the filars are present within a central lumen of the lead body layer such as a central lumen 150' of the inner tubing 146'.

As can be seen in FIG. 17, the remainder of the lead is the same. As the clink 124, connectors 128, 132, and so on are located on the inner tubing 146' of this example, the inner tubing 146' includes the filar passageways 153, 154, 156, and so on discussed above in relation to the lumen body of the previous medical lead example 110. Thus, the construction process for this medical lead example 110', including the process of connecting filars 112 to the clink 124 and connectors 128, 132, and so on proceeds in the same manner as discussed above, albeit without the step of abutting the lumen body 148 to the inner tubing 146'. Instead, the coiled filars 112 are placed within the lead body lumen 150' so that the longitudinally straight portions 160 are present within the inner tubing 146'. The technician then putts each filar from the central lumen 150' of the lead body and through the corresponding filar passageway to the corresponding clink 124 or connector 128, 132.

For medical lead embodiments that may include straight filar ends to a coiled set of Mars but lack a lumen body, a lumen tool 500 such as the example shown in FIGS. 18-22 may be used during a coiling process. Furthermore, for medical lead embodiments that may include straight filar ends of a coiled set of filars and include a lumen body but do not use the lumen body during the coiling process, the lumen tool 500 may be used in place of the lumen body during the coiling process.

The lumen tool 500 is used to hold the ends of the filars being coiled in a longitudinally straight and circumferentially spaced arrangement while the remainder of each filar is coiled. The lumen toot 500 includes an outer body 502, an inner body 506 surrounded by the outer body 502, and one or more end caps 504, 520. The outer body 502 holds the end caps 504, 520 to the inner body 506 such as by a press fit within the outer body 502. The outer body 502 of this particular example may be constructed of a variety of materials including any metal or plastic that has adequate strength to retain the inner body 506 and end caps 504, 520.

The end caps 504, 520 may be made of a relatively soft material such as polyacetal while the inner body 506 may be made of a more rigid material that resists twisting during coiling, such as aluminum. The endcap 504 includes a set of holes 514 that correspond to the desired location of each filar. The endcap 504 also includes a center lumen 516 that can receive a mandril of a coiling machine, which is discussed below in relation to FIGS. 23A-C. The relatively soft material for the end caps 504, 520 allows the filars 112 to experience less stress where the films pass into the holes 514.

Each individual filar 112 is inserted into a corresponding hole 514. The filar may have a relatively small diameter such as on the order of 0.0035 inches while the hole 514 may also have a relatively small diameter such as on the order of 0.004 to 0.0045 inches. Thus, passing the filar 112 directly into the corresponding hole 514 may be difficult.

To ease this insertion process, the end cap 504 may include a series of radial spines 510, 512 that provide surfaces parallel to the longitudinal axis of the tool 500 while also defining a wedged shaped surface 518. The wedged shaped surface 518 may be sloped in the longitudinal direction. In this manner, each wedge shaped surface 518 funnels down to a particular hole 514. Thus, the filar 112 may be directed toward the wedge shaped surface 518 which is a much larger target than the hole 514, and the wedge shaped surface 518 together with the radial spines 510, 512 funnel the filar 112 into the hole 514.

The inner body 506 may be relatively lengthy compared to the diameter of the hole 514. Furthermore, the inner body 506 includes filar holes 522 and a central lumen 517 that align with the holes 514 and central lumen 516 of the end caps 504, 520. These filar holes 522 and central lumen 517 run the length of the inner body 506. Creating the inner body 506 from a relatively rigid material such as a metal may require that the holes 517 and 522 be made in the body 506 in a manner other than drilling. To ease this manufacturing process, the inner body 506 may include radial slots 508 that lead to the holes 572.

Figure 22:
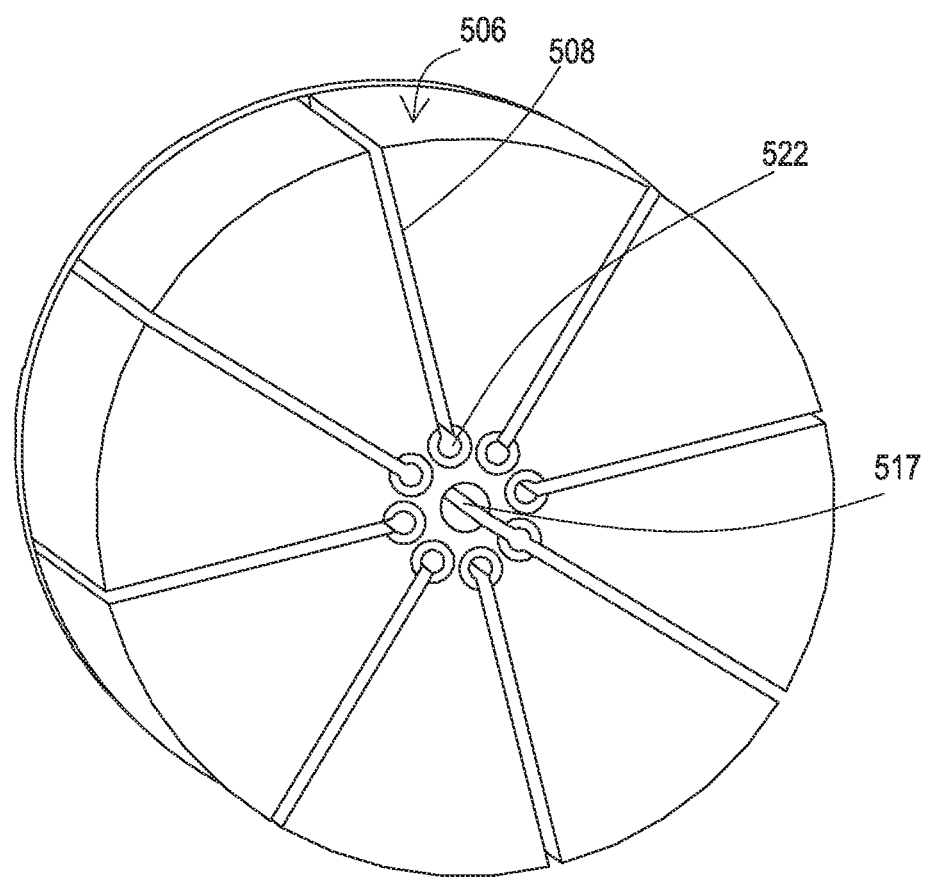
FIG. 22 shows a distal end view of a main body of the tool with the outer cover removed.

As can best be seen in FIG. 22, these radial slots 508 may be created by an electrical discharge machining (EDM) process. The radial slots 508 are cut during EDM so that a cutting wire of the EDM process may be moved radially inward through the body 506 in order to ultimately machine the holes 522. Furthermore, one of the slots 508 may continue radially beyond the filar hole 522 to further machine the central lumen 517.

An alternative construction of the inner body 506 may mimic the lumen body 404 of FIG. 14C. In this case, a hypotube is press fit into a central lumen of the inner body 506 to complete the formation of the holes 522.

Figure 23A:
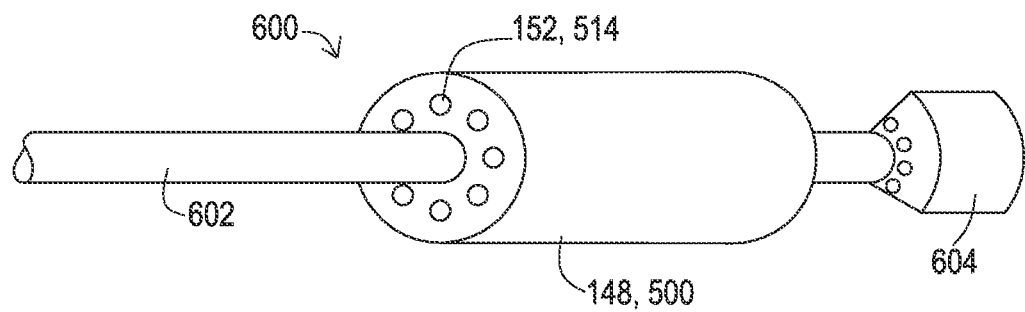
FIG. 23A shows a coiling device that includes either a tool or lumen body to create longitudinally straight ends for filars being coiled on the coiling device.
Figure 23B:
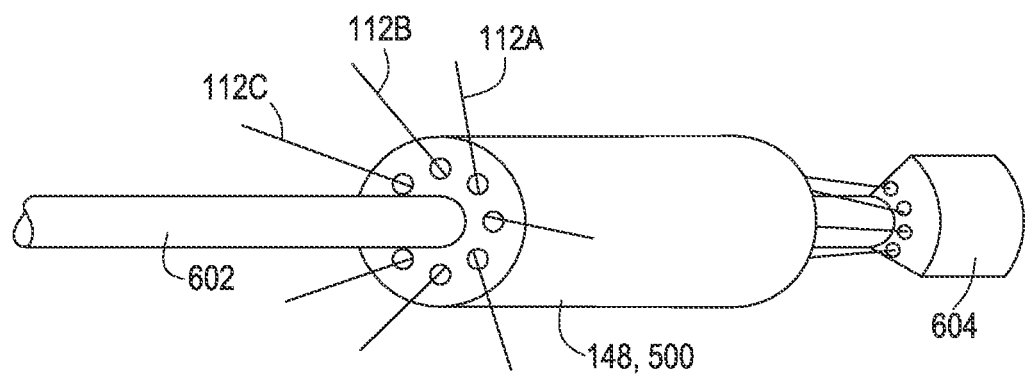
FIG. 23B shows the filars with ends placed through the tool or lumen body and fixed to a chuck before coiling of the filars begins.
Figure 23C:
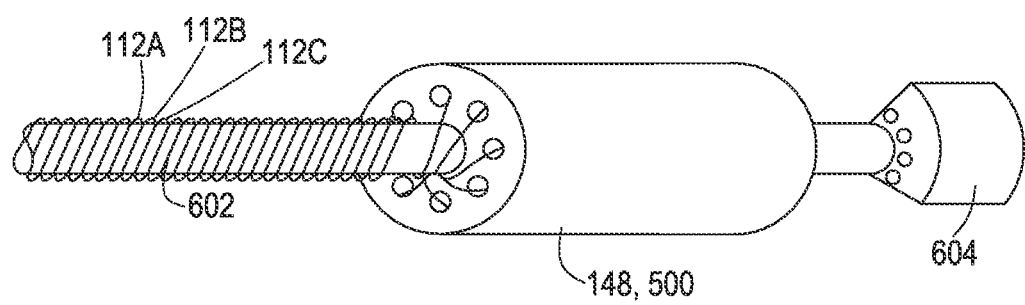
FIG. 23C shows the filars being coiled about a mandril while the ends of the coils are maintained in a longitudinally straight configuration by a tool or lumen body.

FIGS. 23A-23C illustrate one example of a coiling process and system 600 that may be used to created coiled filars with longitudinally straight ends. This system includes a chuck 604 and a mandril 602 where rotation occurs between the chuck 604 and mandril 602 relative to filar spools while Mars are fed onto the mandril 602 from the filar spools. For sets of filars that are coiled end-to-end such as for conventional medical leads, the filars may be attached to the chuck 604 and are then directly fed onto the mandril 602 creating a coil that starts immediately. However, for embodiments of the medical leads 110, 110' that include filars 112 with longitudinally straight ends, either the lumen body 148 or the tool 500 are positioned on the mandril 602 adjacent the chuck 604.

Once the lumen body 148 or tool 500 is positioned on the mandril 602, each filar 112A, 112B, 112C and so on is inserted into a corresponding filar lumen of the lumen body 148 or a filar hole 514 of the endcap 504 of the tool 500. Each filar is fed through the lumen body 148 or tool 500 until exiting at the chuck 604 where the end of each filar may then be secured. Rotation is then created for the combination of the chuck 604, lumen body 148 or tool 500, and the mandril 602 relative to the filars 112A, 112B, 112C, and so on as these filars are fed from wire spools onto the mandril 602.

The filars 112A, 112B, 112C and so on are thereby coiled about the mandril 602 while the portions of the filars 112A, 112B, 112C and so on that are present within the lumen body 148 or tool 500 are maintained with a longitudinally straight configuration.

Once the coiling is complete the coiled filars 112A, 112B, 112C and so on may be removed from the chuck 604 and mandril 602 such as by releasing the coils from the chuck 604 and sliding them off of a free end of the mandril 602. In the case where the lumen body 148 has been used in the coiling process, the lumen body 148 may be removed together with the filars by also sliding the lumen body 148 off of the free end of the mandril 602 while maintaining the longitudinally straight ends of the filars in place within the lumen body 148. The medical lead 110 may then be constructed as discussed above.

In the case where the tool 500 has been used in the coiling process, the filars may be released from the chuck 604 and slid off of a free end of the mandril 602 while the tool 500 remains in place on the mandril 602. The filars slide out of the holes 514 of the tool and have longitudinally straight ends that are otherwise uncontained until they are installed within the lead body. As an alternative, the tool 500 may be removed from the mandril as the filars are removed, and then the filars may be removed from the tool 500. The tool 500 may then be reused to create coiled filars with straight ends for another lead.

While embodiments have been particularly shown and described, it will be understood by those skilled in the art that various other changes in the form and details may be made therein without departing from the spirit and scope of the invention.

What is claimed is:

1. A medical system, comprising:
an implantable medical device including stimulation circuitry connected to a plurality of electrical contacts;
an implantable medical lead comprising:
a plurality of electrical connectors, each electrical connector in contact with a corresponding electrical contact of the plurality of electrical contacts,
a plurality of filars;
a lumen body having a plurality of filar lumens with a filar of the plurality present in each filar lumen where each filar has a longitudinally straight portion present within each filar lumen, the filar lumens being longitudinally straight, each filar extending through a filar passageway within the lumen body and being electrically connected to a corresponding electrical connector,
a lead body joining the lumen body with the filars extending from the lumen body into the lead body, the filars being coiled within the lead body, and
a set of electrodes located on the lead body, each electrode being connected to a corresponding filar.

2. The medical system of claim 1, wherein the lumen body and the lead body are collinear.

3. The medical system of claim 1, wherein the lead body includes a single lumen containing the set of filars.

4. The medical system of claim 1, wherein at least a portion of the lead body abuts a distal end of the lumen body.

5. The medical system of claim 4, wherein the lead body comprises an inner tubing that forms the portion that contacts the lumen body.

6. The medical system of claim 5, further comprising an outer tubing that surrounds at least a first portion of the inner tubing.

7. The medical system of claim 6, further comprising a clink that surrounds a portion of the lumen body and at least a second portion of the inner tubing and that contacts the outer tubing.

8. The medical system of claim 1, wherein the filar passageways are offset circumferentially and longitudinally from each other.

9. The medical system of claim 1, further comprising a plurality of spacers on the lumen body, each spacer being located between a pair of connectors.

10. The medical system of claim 9, wherein the spacers are injection molded and then reflowed.

11. The medical system of claim 1, wherein the lumen body has a center lumen, the medical lead further comprising a stiffening tube disposed within the center lumen.

12. A medical system, comprising:
an implantable medical device including stimulation circuitry connected to a plurality of electrical contacts;
an implantable medical lead comprising:
a plurality of electrical connectors, each electrical connector in contact with a corresponding electrical contact of the plurality of electrical contacts,
a plurality of filars;
a lumen body having a plurality of filar lumens with a filar of the plurality present in each filar lumen, the filar lumens being longitudinally straight, each filar extending through a filar passageway within the lumen body and being electrically connected to a corresponding electrical connector,
a lead body joining the lumen body with the filars extending from the lumen body into the lead body, the filars being coiled within the lead body,
a set of electrodes located on the lead body, each electrode being connected to a corresponding filar, and
an outer tubing that surrounds at least a first portion of the inner tubing,
wherein at least a portion of the lead body abuts a distal end of the lumen body and wherein the lead body comprises an inner tubing that forms the portion that contacts the lumen body.

13. The medical system of claim 12, further comprising a clink that surrounds a portion of the lumen body and at least a second portion of the inner tubing and that contacts the outer tubing.

* * * * *